United States Patent [19]

Woog

[11] Patent Number: 5,062,795
[45] Date of Patent: Nov. 5, 1991

[54] THERAPEUTICALLY CARING FOR THE MOUTH AND THROAT

[76] Inventor: Philippe G. E. Woog, Villa Le Sequoia, Vesenaz, Switzerland

[21] Appl. No.: 504,695

[22] Filed: Apr. 4, 1990

Related U.S. Application Data

[63] Continuation of Ser. No. 64,659, Jun. 22, 1987, abandoned.

[51] Int. Cl.$^5$ ............................................. A61G 17/02
[52] U.S. Cl. ........................................ 433/80; 128/66
[58] Field of Search .............. 128/66, 65, 62 A, 62 R; 433/80, 88

[56] References Cited

U.S. PATENT DOCUMENTS

| | | | |
|---|---|---|---|
| 3,227,158 | 1/1966 | Mattingly | 128/66 |
| 3,863,628 | 2/1975 | Vit | 433/88 |
| 3,870,039 | 3/1975 | Moret et al. | 128/66 |
| 4,699,589 | 10/1987 | Friedman et al. | 128/66 |

Primary Examiner—Gene Mancene
Assistant Examiner—Adriene B. Lepiane
Attorney, Agent, or Firm—Kane, Dalsimer, Sullivan, Kurucz, Levy, Eisele and Richard

[57] ABSTRACT

A method and apparatus for moisturizing and therapy of the mouth and throat is disclosed. A nebulized fine pulsating liquid spray of relatively small droplets is applied. The pressure and temperature of the spray are controlled to obtain optimum penetration. A liquid pulse generator and moisturizing break-up nozzle are employed for practicing the method.

11 Claims, 2 Drawing Sheets

THERAPEUTICALLY CARING FOR THE MOUTH AND THROAT

This is a continuation of copending application Ser. No. 064,659, filed on June 22, 1987, abandoned.

BACKGROUND OF THE INVENTION

It has been demonstrated that rinsing of the oral cavity and gargling of the throat has its limitations in cleansing and delivering solutions to all surfaces of the teeth, gums and cavity walls. Furthermore, there is a constant flow of bacteria containing material (i.e. saliva) back and forth between the oral cavity and the throat and tonsil and pharyngeal areas, and devices aimed at cleaning the oral cavity do not clean the throat and tonsil area and vice versa. Accordingly, reduction of plaque, infection and inflammation cannot be assured. Simple rinsing can actually destroy the delicate balance necessary for the healing process to take place particularly in the early stages of healing. In this connection, tissue defects due to wounding are eventually filled with new connective tissue formed by the advancement of fibroblasts which add new collagen to that deposited previously. The budding capillaries which provide nutriment to this newly developing tissue (and which they cannot do without for this reason) are extremely fragile, blind-ended structures in which blood flow is stagnate or at best merely reciprocating excursions of single cells. Eventually these capillary buds meet and form arches of capillaries and continuous circulation is established just behind the advancing fibroblasts where the recently deposited collagen provides vital structural support for these very friable youthful capillaries enabling them to withstand the pressure of the flow of blood. The regenerating capillaries of the advancing front may be accomplishing their task under very precarious conditions for they must outrun their own circulation and hold a narrow course between the risk of asphyxia and the risk of bursting. The new capillaries cannot exist beyond the furthest fibroblast and in fact, must lag behind. And, they are supported only by this very freshly formed, newly developing tissue. Thus, the need for delicate handling is obvious. Average rinsing/gargling is far from a gentle action.

Antimicrobials, particularly in the form of antiseptic mouth washes and lozenges are widely used in the public. The purposes for such use are diverse, as are the organisms against which they are employed and the types of antimicrobials employed in the various solutions.

A number of these agents have demonstrated efficacy against:
1. Dental plaque
2. Gingival/periodontal inflammation
3. Post surgical complications
4. Tonsilar and other otolaryngeal inflammation/infections.

The formerly developed Woog Orajet has provided an apparatus whereby water and, where desirable, medicament or antibacterial agents are delivered very efficaciously as a sprayer fractionated jet. This prior device is an improvement over the prior art Mono-jet stream for rinsing, however, even this may interrupt the delicate balance of tissue in the early states of healing.

SUMMARY OF THE INVENTION

A principal object of the present invention is to provide an apparatus for therapeutically caring for the mouth and throat.

An additional object is to provide a device which is capable of killing bacteria in both the oral cavity and in the throat, tonsil and pharyngeal areas, and thus stop the movement back and forth of bacteria containing materials between these areas.

Another object is to provide an apparatus of the foregoing type whereby the particles are not only fractionated but actually nebulized. This nebulization will provide additionally superior efficacy after surgery in the mouth but also and more specifically for therapy of the throat.

The irrigation/nebulizer can provide such advanced efficacy because among other activities the invention produces an acceleration of blood flow to the gingival and periodontal tissue providing a better milieu for healing; acceleration of blood flow provides a better and more abundant supply of nutriment and oxygen to the tissue, both substances required for maintenance of tissue health, healing if inflammation and/or infection are present and advantageous conditions for containment and destruction of infectious organisms; specifically better crevicular fluid flow provides an increased opportunity for emergence of polymorphonuclear leukocytes (the infection fighting white blood cells), immunoglobulins and compliment to play their role in continuing the health of, or fighting infectious organisms which might become lodged in, the crevicular tissue.

The newly-designed apparatus, because it proceeds even further so as not only to fractionate the jet of water into numerous microparticles but further into a fine mist spray not only can accomplish all of the factors listed, but offers additional therapeutic aid in that:

1. It can penetrate areas which are even more inaccessible to larger particles thus providing a healing effect not otherwise obtainable.

2. It can provide an aid to healing after periodontal surgery above and beyond that otherwise obtainable.

The mist tip of the irrigation/nebulizer of this invention could provide even greater therapeutic efficacy to the oral and oropharyngeal areas because:

1. It can carry antimicrobial solutions into areas of gingival inaccessibility to fight infection which is always a problem in these areas.

2. It can provide the same, and more, efficacious delivery of cleansing and/or antimicrobial action into the pharyngeal areas where a problem constantly may exist. Tonsilar tissue presents innumerable inaccessible crannies and crevices which can be treated only with extreme difficulty and use of rinsing/gargling/lozenges leaves many of these untouched. Application of the fine spray provided at high speeds of nebulization by the nozzle of this invention allows penetration of these difficult or impossible-to-reach areas.

3. Applications of the fine mist provided by the nozzle of this invention also presents a safety feature not present in the rinse/gargle method. A number of reports exist in the literature of adverse effects from injudicious use of an antiseptic/therapeutic/antimicrobial solution. The nozzle of this invention provides for safe use of a minimal amount of such solutions to effect the same or better results than those which would be provided by a mouthwash/gargle. The device allows for cleaning of both the oral cavity and the throat and pharyngeal areas and thus provides a means of preventing the flow of bacteria containing material (i.e. saliva) back and forth between these areas.

DETAILED DESCRIPTION OF THE INVENTION

Figure 1:
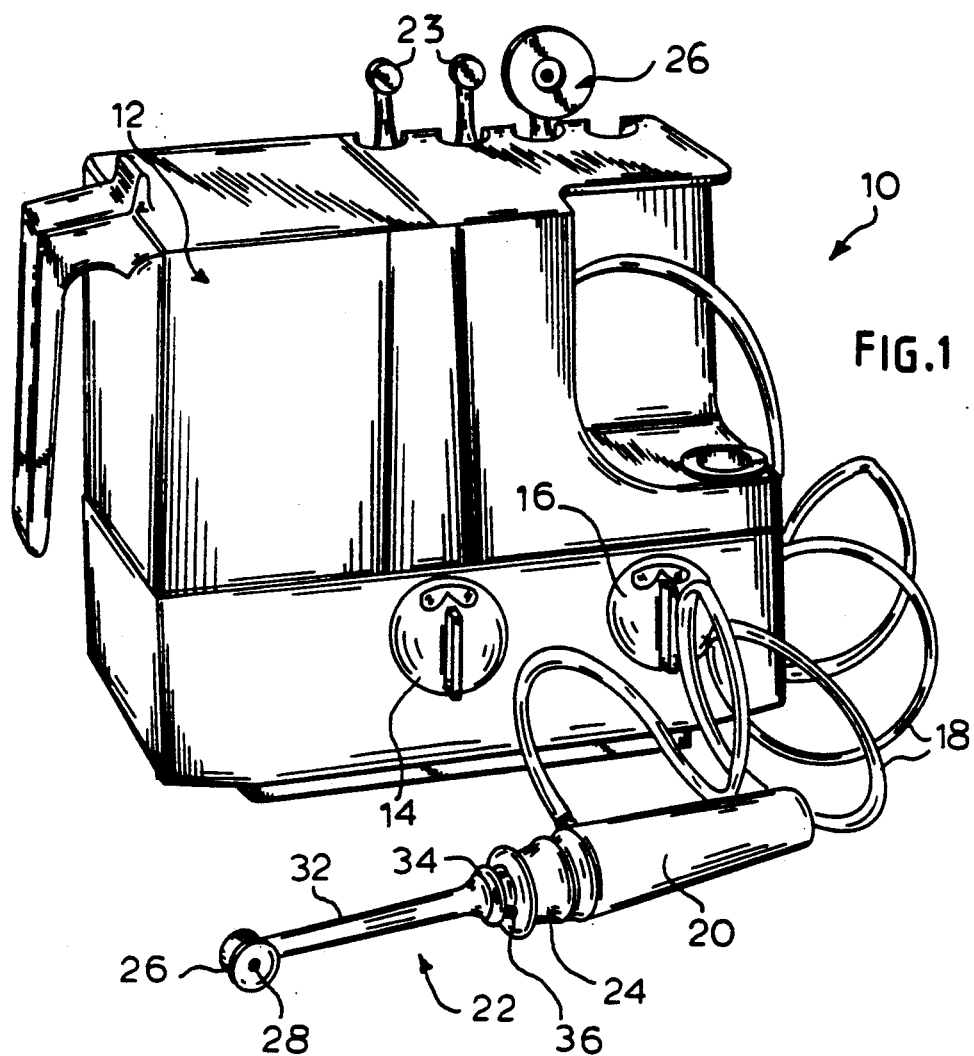
FIG. 1 is a perspective view of a liquid pulse generator having a moisturizing nozzle and a fractionated et nozzle connected thereto.
Figure 2:
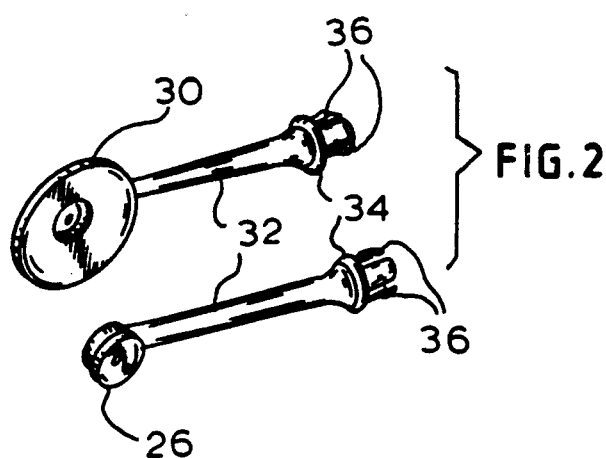
FIG. 2 is a perspective view of a moisturizing nozzle for emitting a fine spray.
Figure 3:
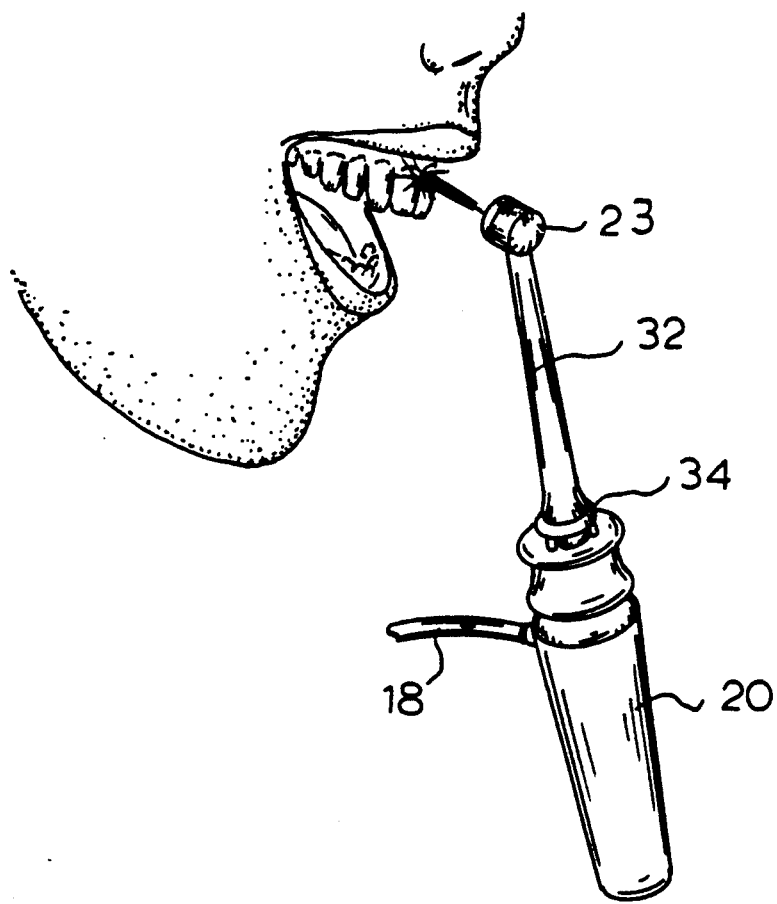
FIG. 3 is a perspective view of the method of using the fractionated jet nozzle according to the invention.

The apparatus employed for practicing the method according to the invention is shown in FIG. 1. A liquid pulse generator 10 is provided together with a liquid reservoir 12 mounted thereon. It has been found that liquid pulse generators as commonly employed with oral hygiene devices are suitable for practicing the invention. The mechanisms for producing liquid pulses are well known and a detailed description thereof is not considered necessary for fully appreciating the present invention. The fractionated jet nozzle 23 is also employed for oral hygiene.

The generator 10 includes an on/off switch 16 and a dial 14 for setting the pressure of the liquid pulses. A tube 18 is connected to the generator 10 for conveying liquid therefrom. A handle 20 is connected to the tube and a moisturizing nozzle attachment 22 is secured to the handle. A manually operated control member 24 may be pushed forward to open a valve within the handle and supply the liquid pressure pulses to the nozzle attachment 22. A comparable handle is disclosed in U.S. Pat. Nos. 3,851,643 and 4,159,715. The fractionated jet nozzle 23 is also employed for oral hygiene.

The nozzle attachment 22 includes a break-up nozzle 26 having a pin-hole opening 28 for emitting a fine mist. A washer 30 having a central opening may be fitted about the nozzle 26. The nozzle attachment 22 includes a hollow shaft 32 having a shoulder 34 near its lower end. A pair of projections 36 extend downwardly from the shoulder 34 and snap within the handle 20.

The liquid pulse generator 10 is capable of providing between 500 and 5000 pulses per minute. A peak internal pressure as high as 10 kg/cm² can be achieved for maximum penetration. The internal pressure range of the generator is between 2.5 and 10 kg/cm² (peak value) with a mean average value between 1.5 and 3.0 kg/cm².

It is important that the liquid discharge rate be kept to a minimum. A pulsating system is most desirable in this regard. The nozzle 26 is designed to emit between 10 and 100 milliliters/minute when the generator is providing pulsations of water in the desired pressure range.

Figure 4:
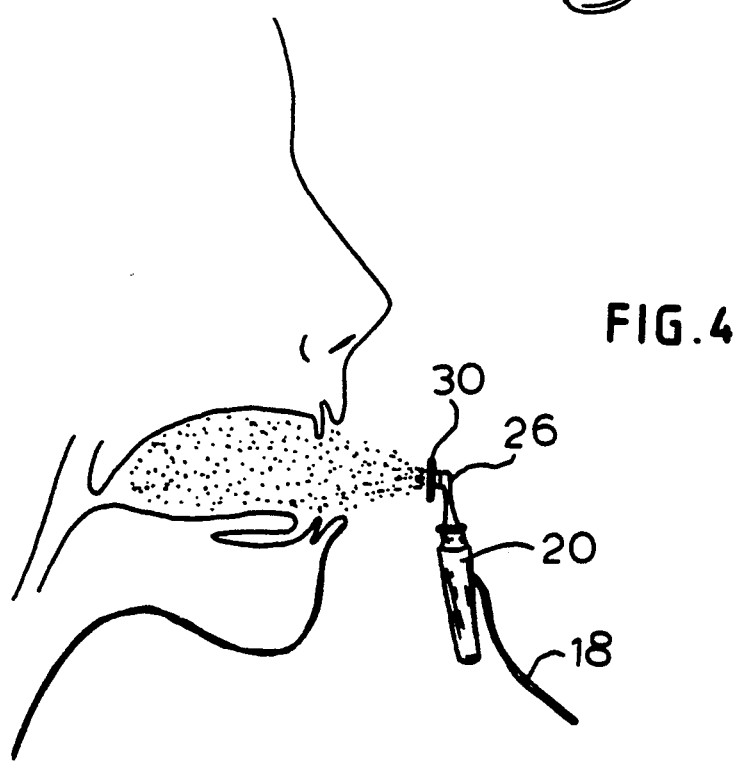
FIG. 4 is a perspective view of the method of using the moisturizing nozzle according to the invention.

The moisturizing apparatus according to the invention is employed in the manner shown in FIG. 4. The reservoir 12 is first filled with water having a temperature of about 27° C. to 50° C. Where desired a prescribed antimicrobial solution or other therapeutic agents or medicaments may be added. In this connection, antibacterial agent Chlorehidine under tradename Peridex has received acceptance for use in mouth by FDA. This product is good as an antibacterial agent for the mouth especially when a person has tonsillitis. Most other antibacterial agents cannot reach outer layers of tonsillitis. If Chlorihidine is used in certain dilution with jet pulse an effective rinse is obtained. When a nebulizer spray of 2 or 3 seconds is used tonsils may be reached.

Switches 16 and 14 are set to provide pulsations of water at the desired pressure. The control member 24 is pushed to permit liquid to pass from the hose 18 to the nozzle. A fine mist is rapidly emitted for a desired period, generally between 1 to 10 seconds.

The apparatus is convenient in that the nozzle may be easily manipulated by the user. The flexible tube 18 allows the nozzle to be positioned at the necessary orientations to moisturize all parts of the oral cavity and throat. Since only a fine mist is emitted, there is no excess water to inconvenience the user.

The nozzle is adjusted so that the mist being emitted therefrom comprises water droplets which are small enough to prevent harm to oral tissue. Thus, these water droplets can range from 10-70 microns in diameter. Preferably they have a diameter of 20-50 microns.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

What is claimed is:

1. An apparatus for wound lavage and for moisturizing and therapy of the oral cavity and throat, comprising:
   a liquid pulse generator;
   a spray break-up nozzle connected to said liquid pulse generator including means for setting a discharge rate of said nozzle to between 10 and 100 ml/minute and a pin-hole discharge opening designed for emitting a nebulized fine spray pattern of relatively small droplets in the form of fine mist under pressure and consisting essentially of liquid droplets small enough to prevent harm to tissues of the mouth and throat.

2. The apparatus as defined in claim 1 including means for providing a spraying pressure having a peak value between 2.5 and 10 kg/cm².

3. The apparatus of claim 1 wherein said liquid droplets have a diameter of 20-50 microns.

4. A method for wound lavage and for moisturizing and therapy of the mouth and throat, the steps comprising:
   spraying all parts of the oral cavity of the mouth and throat with a pulsating nebulized fine liquid spray of relatively small droplets in the form of fine mist under sufficient pressure from a break-up nozzle and consisting essentially of water droplets small enough to prevent harm to tissues of the mouth and throat.

5. The method as defined in claim 4 wherein said liquid spray is sprayed under a peak pressure range between 2.5 and 10 kg/cm².

6. The method as defined in claim 4 wherein the mouth and throat is sprayed at between 10 and 100 ml/minute.

7. The method as defined in claim 6 wherein the temperature of said spray is 27° C. to 50° C.

8. The method of claim 6 wherein said pulsating fine liquid spray consists essentially of water droplets having a diameter of 10-70 microns.

9. The method as defined in claim 4 including the step of spraying the mouth and throat with between one thousand and three thousand pulsations per minute.

10. The method as defined in claim 4 wherein the temperature of said spray is 27° C. to 50° C.

11. The method of claim 4 wherein said pulsating fine liquid spray consists essentially of water droplets having a diameter of 10-70 microns.

* * * * *